United States Patent [19]

Huang et al.

[11] Patent Number: 4,482,544
[45] Date of Patent: Nov. 13, 1984

[54] COMPOUNDS FOR TREATING HYPERTENSION

[75] Inventors: Fu-chih Huang, Boonton, N.J.; Howard Jones, Ossining; Wan-Kit Chan, Yorktown Heights, both of N.Y.

[73] Assignee: USV Pharmaceutical Corporation, Tarrytown, N.Y.

[21] Appl. No.: 445,117

[22] Filed: Nov. 29, 1982

[51] Int. Cl.³ .................... A61K 37/00; C07C 103/52
[52] U.S. Cl. .............................. 424/177; 260/112.5 R
[58] Field of Search .................. 424/177; 260/112.5 R

[56] References Cited
U.S. PATENT DOCUMENTS 4,374,829  2/1983  Harris et al. ..................... 424/177

FOREIGN PATENT DOCUMENTS 2095682  10/1982  United Kingdom ......... 260/112.5 R

Primary Examiner—Delbert R. Phillips

[57] ABSTRACT

Compounds of the general formula

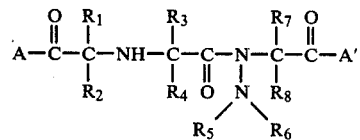

and their pharmaceutically-acceptable salts, wherein the substituents are as defined herein, having antihypertensive activity.

17 Claims, No Drawings

COMPOUNDS FOR TREATING HYPERTENSION

BACKGROUND OF THE INVENTION

This application relates to compounds, their pharmaceutically acceptable salts, and pharmaceutical preparations made therefrom, having biological activity as inhibitors of the enzymatic conversion of angiotensin I to angiotensin II. As such, the products comprising the present invention have utility in the treatment of hypertension in subjects suffering therefrom.

SUMMARY OF THE INVENTION

Broadly stated, the present invention comprises compounds of the formula

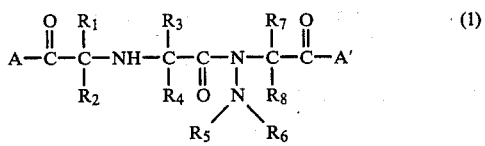

and their pharmaceutically-acceptable salts, wherein

A and A' are independently hydroxy, alkoxy, alkenoxy, aryloxy, arylalkylamino, or hydroxyamino;

$R_1$, $R_2$, $R_7$, and $R_8$ are independently hydrogen, alkyl, aryl, aralkyl, fused cycloalkyl-aryl, fused arylcycloalkyl, aryloxyalkyl, or arylalkyloxyalkyl;

$R_3$ and $R_4$ are independently hydrogen, lower alkyl, lower alkenyl, lower alkynyl, aryl, fused cycloalkyl-aryl, fused aryl-cycloalkyl, fused cycloalkylaryl-alkyl, fused arylcycloalkyl-alkyl, aralkyl, cycloalkyl, or heterocyclic;

$R_5$ and $R_6$ are independently hydrogen, alkyl, alkenyl, alkynyl, acyl, cycloalkyl, cycloalkyl-alkyl, polycycloalkyl, polycycloalkyl-alkyl, aryl, aralkyl, fused cycloalkyl-aryl, fused arylcycloalkyl, fused aryl-cycloalkyl-alkyl, or fused cycloalkyl-aryl-alkyl, or $R_5$ and $R_6$ may be connected together to form with the nitrogen to which they are attached a saturated or unsaturated ring containing from 2 to 9 carbon atoms and optionally an oxygen atom, sulfur atom, or second nitrogen atom, wherein the ring can be substituted with hydroxy, alkyl, alkoxy, aryl, aryloxy, aralkyl, or mono- or dialkylamino, and can be fused with another aryl or cycloalkyl ring which can be substituted with hydroxy, alkyl, alkoxy, aryl, aryloxy, aralkyl, or mono- or dialkylamino;

wherein the alkyl, alkoxy, alkenoxy, alkenyl, and alkynyl groups may carry substituents selected from the group consisting of hydroxy, acyloxy, aryl, alkoxy, aryloxy, halo, amino, mono- or dialkylamino, acylamino, thio, and alkylmercapto; the cycloalkyl rings may include a hetero atom, may be saturated or unsaturated, and where not fused with both $R_5$ and $R_6$ may carry substituents selected from the group consisting of alkyl, halo, haloalkyl, hydroxy, alkylamino, and nitro; and the aryl rings may contain a hetero atom and where not fused with both $R_5$ and $R_6$ may carry substituents selected from the group consisting of carboxylic acid, cyano, carbo-lower alkoxy, alkyl, hydroxy, alkoxy, hydroxyalkyl, halo, haloalkyl, thio, alkylmercapto, thioalkyl, amino, alkylamino, aminoalkyl, nitro, methylenedioxy, and sulfonylamino;

wherein the alkyl groups contain 1 to 9 carbon atoms; and the cycloalkyl groups and the cycloalkyl portions of substituents containing cycloalkyl groups contain 3 to 9 carbon atoms.

DESCRIPTION OF THE PREFERRED EMBODIMENTS

Preferred compounds of the present invention are those of the general formula given above in which A and A' are each hydroxy or lower alkoxy; $R_1$, $R_2$, $R_3$, $R_4$, $R_7$ and $R_8$ are each hydrogen, alkyl, aryl, or w-amino alkyl wherein the amino is mono- or disubstituted with hydrogen, alkyl, aryl, or aryl alkyl, or is incorporated in a saturated or unsaturated one- or two-ring heterocyclic moiety containing preferably up to 12 atoms in the ring; and $R_5$ and $R_6$ are independently hydrogen, alkyl, aryl, or cycloalkyl, or are joined together to form an alkylene or hetero-alkylene bridge or fused aralkylene, in which the alkyl, aryl, cycloalkyl, bridge, and fused aralkylene can be substituted or unsubstituted. Included as preferred groups are groups in which $R_5$ or $R_6$ provide diuretic activity to the compound (1), e.g., sulfonamido-chlorophenyl.

The alkyl groups per se and the alkyl moieties in alkoxy, aralkyl, cycloalkyl, aminoalkyl, and the like, may be straight-chained or branched and preferably contain from 1 to 9 carbon atoms. Such groups include methyl, ethyl, propyl, isopropyl, butyl, isobutyl, tertiary-butyl, amyl, iso-amyl, hexyl, octyl, and the like. Preferably the alkyl groups are lower alkyl, which term shall refer to alkyl groups containing from 1 to 6 carbon atoms, straight-chained or branched.

The alkenyl and alkynyl groups and moieties can also be straight- or branched-chained groups containing from 2 to 9, and preferably 2 to 6, carbon atoms. Such groups include vinyl, ethynyl, propenyl, isopropenyl, and the like.

The acyl groups include such groups as alkanoyl, aroyl, and aralkanoyl, wherein the alkyl and aryl moieties are as defined herein, as well as sulfonyl, sulfamoyl, carbamoyl, and the like, optionally containing an alkyl moiety with 1 to 9 and preferably 1 to 6 carbon atoms.

The preferred substituents on the above alkyl, alkenyl, alkynyl, and acyl groups include hydroxy, alkoxy, amino, alkylamino, dialkylamino, mercapto, alkylmercapto, halo, and the like.

The cycloalkyl groups and moieties are saturated or unsaturated and preferably contain 3 to 9 carbon atoms. By "polycycloalkyl" is meant 2 or more fused cycloalkyl rings, having a total of up to 20 carbon atoms. The cycloalkyl, polycycloalkyl, and fused aryl-cycloalkyl structures can also contain a hetero atom, i.e., a sulfur, oxygen, or nitrogen atom, thereby forming a hetero-ring.

Preferred cyclic and polycyclic ring structures include such radicals as cyclopropyl, cyclobutyl, cyclopentyl, cyclohexyl, cycloheptyl, adamantyl, norbornyl, phenyl, tolyl, benzyl, phenethyl, indolyl, dimethoxyphenyl, hydroxybenzyl, indanyl, naphthyl, tetrahydronaphthyl, decanhydronaphthyl, pyridyl, quinolyl, guanidino, pyrrolidyl, pyrrolyl, morpholinyl, furyl, furfuryl, tetrahydrofurfuryl, benzimidazolyl, thienyl, imidazolyl, and the like; of these, the structures containing at least one nitrogen atom are preferred structures for those embodiments in which $R_5$ and $R_6$ are connected to each other. Preferred substituents on the ring structures which can be formed by connecting $R_5$ and $R_6$ include hydroxy, alkyl, alkoxy, aryl, aryloxy, aralkyl, alkylamino, and dialkylamino; these and alkenyl, alkynyl, carboxy, carboalkoxy, cyano, mercapto, amino, alkylmercapto, halo, trifluoromethyl, sulfonamide, and the like, are preferred substituents on all other aryl, cycloalkyl, fused arylcycloalkyl, and polycycloalkyl ring structures.

The halo groups include fluoro, chloro, bromo and iodo.

Substituents which are "unsaturated" contain one or more double or triple bond.

Compounds in accordance with the present invention are readily prepared employing known starting materials and procedures. It will be understood by those skilled in the art that the carbons to which $R_1$ and $R_3$ are attached can be asymmetric centers, such that the inventive compounds may exist in SS, SR, RS, and RR forms. Individual isomers and diastereoisomeric mixtures of said forms are within the scope of the invention. The preferred forms have (S,S) configuration.

The compounds of the formula (1) can be prepared by esterifying a compound of the formula (2):

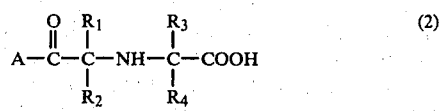

with e.g. isobutylene in dioxane to form compound (3):

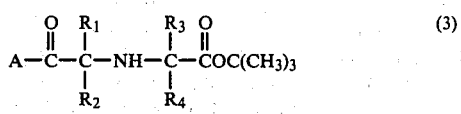

wherein $R_1$, $R_2$, $R_3$, $R_4$, and A are as defined hereinabove. The amino group in compound (3) is then protected, for instance, by reacting compound (3) in pyridine with a suitable protecting group such as 2,2,2-trichloroethyl chloroformate (4):

to form the protected ester compound (5):

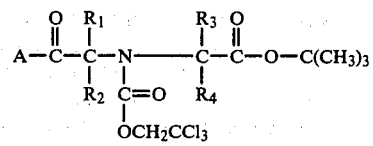

Compound (5) is then de-esterified, and then converted to e.g. the acid chloride, by reacting compound (5) with strong HCl in dioxane, and then reacting the resultant acid (6):

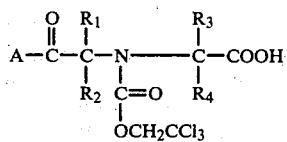

with, for instance, oxalyl chloride in methylene chloride to form compound (7):

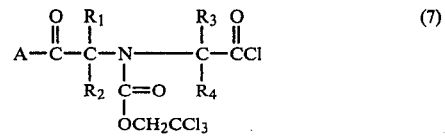

The hydrazine compound with which compound (7) is eventually reacted is formed by reacting compounds of the formula (8):

with e.g. a compound of the formula (9):

to form compound (10):

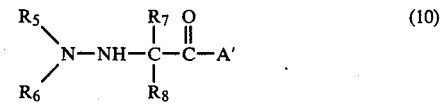

wherein $R_5$, $R_6$, $R_7$, $R_8$, and A' are as defined hereinabove. Compounds (7) and (10) are reacted in a suitable solvent such as methylene chloride/pyridine to form compound (11):

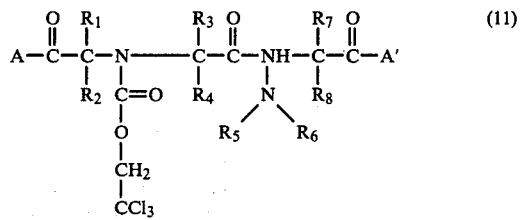

Compound (11) is de-N-protected with e.g. zinc dust in glacial acetic acid to form compound (1). Where A' forms an ester, the product can be converted to the corresponding acid by bubbling HCl through a solution thereof.

Each of the above reactions proceeds in a straightforward manner in a suitable solvent at temperatures ranging from 0° C. to 150° C.

The products are obtained typically as a mixture of diastereoisomers which can be separated by standard methods of fractional crystallization or chromatography.

The compounds of this invention form acid salts with various inorganic and organic acids which are also within the scope of the invention. The pharmaceutically acceptable acid addition salts of the compounds of the present invention may be prepared by conventional reactions by reacting the free amino acid or amino ester with an appropriate acid providing the desired anion, either in a solvent or medium in which the salt is insoluble, or in water and removing the water by freeze-drying. The salts of strong acids are preferred. As exemplary, but not limiting, of pharmaceutically acceptable acid salts are the salts of hydrochloric, hydrobromic, sulfuric, nitric, acetic, fumaric, malic, maleic and citric acids.

The action of the enzyme renin or angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds of this invention intervene in the renin-to-angiotensin I-to-angiotensin II sequence by inhibiting angiotensin I converting enzyme and reducing or eliminating the formation of the pressor substance angiotensin II and therefore are useful in reducing or relieving hypertension. Thus by the administration of a composition containing one or a combination of compounds of formula (1) or pharmaceutically acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but a parenteral route such as subcutaneously, intramuscularly, intravenously or intraperitonealy can also be employed.

When evaluated according to standard, recognized in vivo methods, a compound of the present invention in the (S,S) form and having the structure (5):

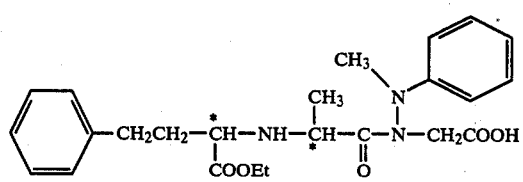

exhibited angiotensin converting enzyme inhibition of 52% and 79% at a dose level of 1 mg/kg. ED$_{50}$ values of less than 1 mg/kg have been exhibited by compounds (5) and (6):

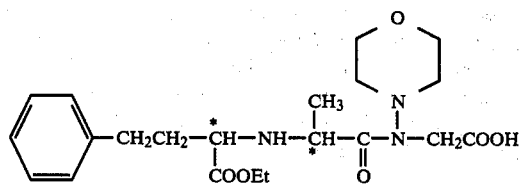

The compounds of the invention can be utilized to achieve the reduction of blood pressure by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

Specific embodiments of the invention are illustrated in the following Examples.

EXAMPLE I

An intermediate employed in the following examples, N-[(1S)-ethoxycarbonyl-3-phenylpropyl]-N-(2,2,2-trichloroethoxycarbonyl)-L-alanine acid chloride,

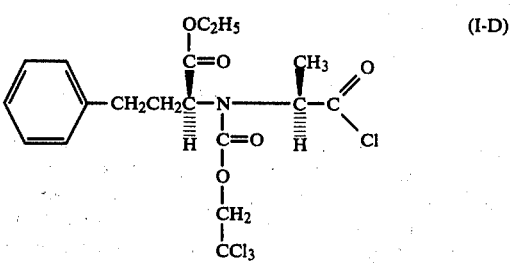

was prepared as follows:

To a mixture of N[(1S)-ethoxycarbonyl-3-phenylpropyl]-L-alanine (10 g) and sulfuric acid (10 ml) in 100 ml of dioxane was added 150 ml of isobutylene, and the resulting reaction mixture was shaken in a pressure bottle overnight. The reaction mixture was neutralized with 50% NaOH, taken up in 200 ml of ethyl acetate, and washed with water. The organic solution was dried and evaporated to dryness to give 10 g of oily product (I-A), N-[(1S)-Ethoxycarbonyl-3-phenylpropyl]-L-alanine t-butyl ester.

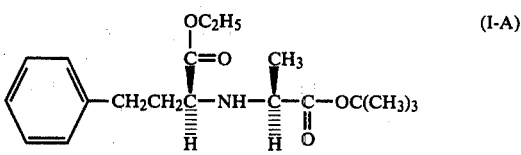

A mixture containing 2.52 g (7.51 mmol) of compound (I-A), 1.10 ml (7.99 mmol) of 2,2,2-trichloroethyl chloroformate, and 1.0 ml (12.4 mmol) of pyridine in 25 ml of dry tetrahydrofuran was refluxed under a nitrogen atmosphere for 3 hours. The reaction mixture was filtered, taken up in 200 ml of ether, and washed four times with 1N hydrochloric acid and once with brine. The organic phase was dried over MgSO₄, filtered, and concentrated in vacuo to yield 3.79 g (99%) of compound (I-B), N-[(1S)-1-ethoxycarbonyl-3-phenylpropyl]-N-(2,2,2-trichloroethoxycarbonyl)-L-alanine t-butyl ester:

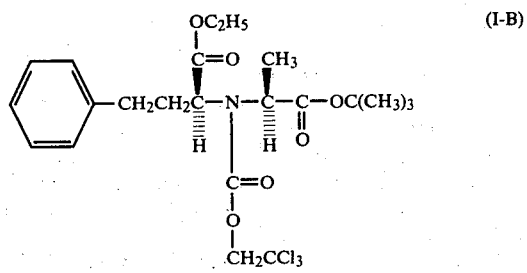

A mixture containing 1.98 g (3.88 mmol) of compound (I-B) in 25 ml of 4N HCl in dioxane at room temperature and under a nitrogen atmosphere was stirred for 8 hours. The mixture was then concentrated in vacuo to provide 1.77 g (100%) of compound (I-C), N-[(1S)-1-ethoxycarbonyl-3-phenylpropyl]-N-(2,2,2-trichloroethoxycarbonyl)-L-alanine:

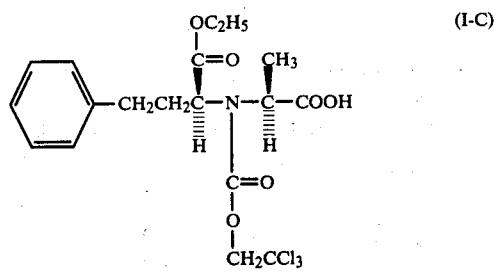

To a mixture containing 908 mg (2.00 mmol) of compound (I-C) and 0.40 ml (4.6 mmol) of oxalyl chloride in 10 ml of dry methylene chloride at room temperature and under a nitrogen atmosphere was added 10 L (0.13 mmol) of N,N-dimethylformamide. After two hours the mixture was carefully concentrated in vacuo (T<30° C.) to give 900 ml of the acid chloride, compound (I-D).

EXAMPLE II

A mixture of 1-methyl-1-phenylhydrazine (5 g, 41 mmol) t-butyl bromoacetate (8 g, 41 mmol), and sodium carbonate (2.2 g, 21 mmol) in 20 ml of DMF was stirred at room temperature overnight. DMF was removed in vacuo. The residue was extracted into ethyl acetate and the organic solution was washed with water, dried and evaporated to give 6.5 g of crude oily product. Purification by dry column chromatography gave 2 g of t-butyl (N'-methyl-N'-phenyl)hydrazinoacetate (compound II-A). A solution of 1.11 g of compound (II-A) and 3 ml of pyridine in 10 ml of methylene chloride was added dropwise to a solution of 2 g of compound (I-D) in 10 ml of methylene chloride. The reaction mixture was stirred at room temperature overnight and was then washed with 1N hydrochloric acid, aqueous sodium bicarbonate, and brine. The organic solution was dried over magnesium sulfate, filtered, concentrated in vacuo, and purified by dry column chromatography to give 1.5 g of slightly impure desired product (II-B), N-(N-methylanilino)-N-[N-[(1S)-1(ethoxycarbonyl)-3-phenylpropyl]-N-(2,2,2-tri-chloroethoxycarbonyl)-L-alanyl]glycine t-butyl ester:

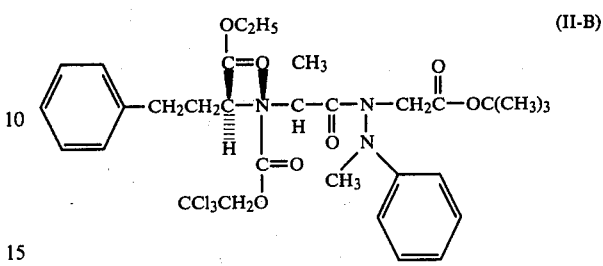

To a solution of 1.5 g of product (II-B) in 10 ml of glacial acetic acid was added 2.5 g of zinc dust. After 2 hours the mixture was filtered through celite and concentrated in vacuo. The residue was taken up in ether and washed successively with sodium bicarbonate solution, water, and brine and dried. After filtration, the solution was concentrated in vacuo and purified by dry column chromatography to give 0.7 g of pure product (II-C), N-(N-methylanilino)-N-[N-[(1S)-1-ethoxycarbonyl-3-phenylpropyl]-L-alanyl]glycine t-butyl ester:

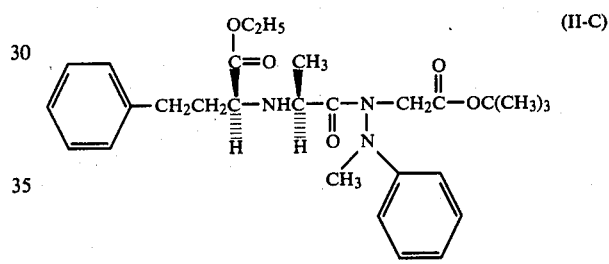

This product was converted to the dihydrochloric acid salt of the free acid by bubbling a stream of hydrogen chloride gas into an etheral solution of 0.7 g of product (II-C) at 0° C. for 3 hours. The solution was concentrated in vacuo to give 0.4 g of white powder.

EXAMPLE III

A mixture of N-aminomorpholine (4 g), t-butyl bromoacetate (7.6 g) and sodium carbonate (2.1 g) in 20 ml of DMF was stirred at room temperature overnight. After concentration in vacuo, the residue was taken up in ethyl acetate. The organic solution was washed with water, dried, filtered and concentrated in vacuo to give 2.5 g of crude N-(morpholino)glycine t-butyl ester (compound III-A). This crude compound was used without further purification. To a solution of 5 g of the product (I-D) in 10 ml of methylene chloride was added a solution of 2.5 g of compound (III-A) and 5 ml of pyridine in 5 ml of methylene chloride over a period of 10 minutes. After 16 hours the reaction mixture was washed successively with 1N hydrochloric acid, saturated aqueous sodium bicarbonate, and once with brine. The organic solution was dried, filtered, concentrated in vacuo, and purified by dry column chromatography to give 3.5 g of oily product (III-B), N-(morpholino)-N-[N-[(1S)-1-ethoxycarbonyl-3-phenylpropyl]-N-(2,2,2-trichloroethoxycarbonyl)-L-alanyl]glycine t-butyl ester:

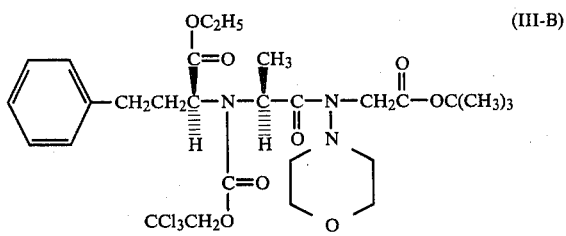

(III-B)

To a solution of 0.6 g of product (III-B) in 10 ml of glacial acetic acid was added 2 g of zinc dust. After three hours the mixture was filtered through celite and concentrated in vacuo. The residue was taken up in ethyl acetate and washed with water. The organic solution was dried, filtered, concentrated in vacuo, and chromatographed to give 0.4 g of product (III-C), N-(morpholine)-N-[N-[(1S)-1-ethoxycarbonyl-3-phenylpropyl]L-alanyl]glycine t-butyl ester:

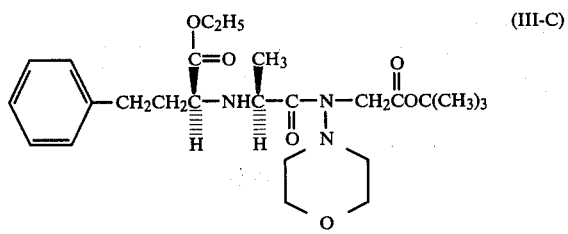

(III-C)

The dihydrochloric acid salt of the free acid was formed by bubbling dry hydrogen chloride gas into an ethereal solution containing 0.5 g of product (III-C) at 0° C. for 2.5 hours. Concentration in vacuo gave 0.4 g of solid product.

EXAMPLE IV

A mixture of 1-amino-2-methylindoline (3.7 g), potassium carbonate (2.8 g) and t-butyl bromoacetate (4 g) in 10 ml of DMF was stirred at room temperature overnight. After removal of DMF in vacuo, the residue was taken up in ethyl acetate. The organic solution was washed with water, dried with magnesium sulfate, filtered, and concentrated. The product was purified by dry column chromatography to give 1.5 g of slightly impure oily product (IV-A), N-[1-(2-methylindolino)]glycine t-butyl ester. This was used for the next reaction without further purification.

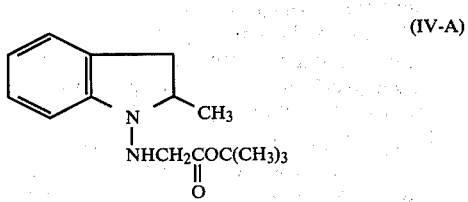

(IV-A)

A solution of 2.25 g of acid chloride product (I-D) in 10 ml of methylene chloride was added dropwise to a 15 ml of methylene chloride solution containing 1.5 g of product (IV-A) and 0.4 g of pyridine over a period of 10 minutes. After 20 hours the reaction mixture was washed successively with 1N hydrochloric acid, saturated aqueous sodium bicarbonate, and brine solution. The organic solution was dried, filtered, concentrated and purified by dry column chromatography to give 2 g of product (IV-B), N-[1-(2-methylindolino)]-N-[N-[(1S)-1-ethoxy-carbonyl-3-phenylpropyl]-N-(2,2,2-trichloroethoxycarbonyl)-L-alanyl]glycine t-butyl ester:

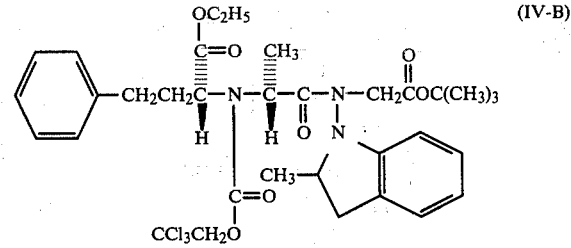

(IV-B)

To a solution of 2 g of the product (IV-B) in 10 ml of acetic acid was added 4 g of zinc dust. After 2 hours the reaction mixture was filtered through celite and concentrated in vacuo. The residue was purified by dry column chromatography to give 0.8 g of oily product (IV-C), N-[1-(2-methylindolino)]-N-[N-[(1S)-1-ethoxycarbonyl-3-phenylpropyl]-L-alanyl]glycine t-butyl ester:

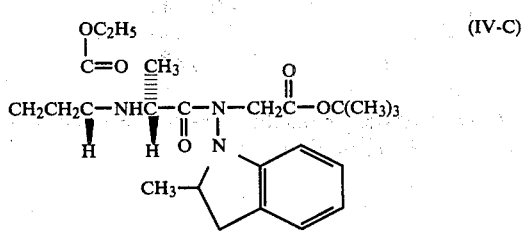

(IV-C)

The dihydrochloric acid salt of the free acid was prepared by bubbling dry hydrogen chloride gas into an etheral solution containing 0.8 g of product (IV-C) at 0° C. for 2 hours. Concentration in vacuo gave 0.4 g of solid product.

EXAMPLE V

The following compounds are prepared by procedures wholly analogous to the procedure used in Example III:

N-(1-piperidino)-N-[N-[(1S)-1-ethoxycarbonyl-3-phenylpropyl]-L-alanyl]glycine t-butyl ester and dihydrochloric acid salt.

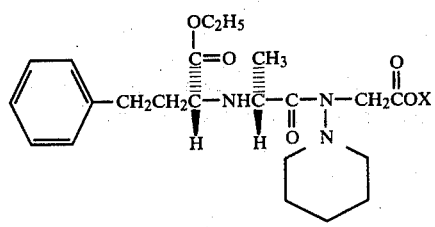

(V-A) X: —C(CH$_3$)$_3$
(V-B) X: —OH.2HCl

EXAMPLES VI–X

The following compounds are made by procedures wholly analogous to the procedure set forth in Examples I and II:

(VI-A)  N-(N-Ethylbenzylamino)-N-[N-[(1S)-1-ethoxycarbonyl-3-phenylpropyl]-L-alanyl]glycine:

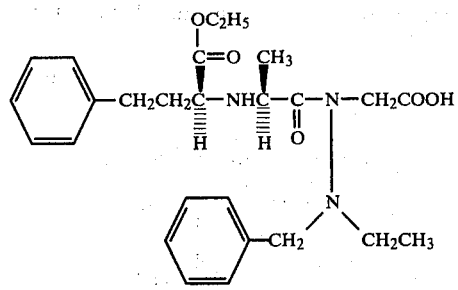

(VII-A)  N-(N-Methylanilino)-N-[N-[(1S)-1-ethoxycarbonyl-3-phenylpropyl]-L-lysinyl]glycine:

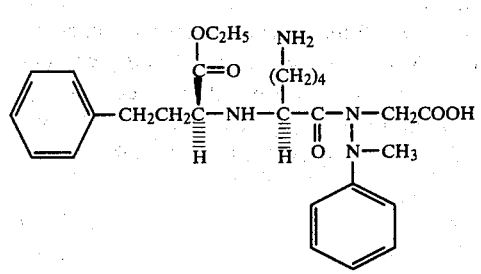

(VIII-A) N-(N-Methylanilino)-N-[N-[(1S)-1-ethoxycarbonyl-ethyl]-L-alanyl]glycine

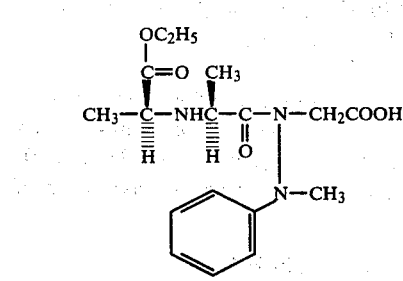

(IX-A) N-(Dimethylamino)-N-[N-[(1S)-1-ethoxycarbonyl-3-phenylpropyl]-L-alanyl]glycine

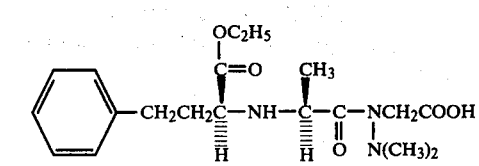

(X-A) N-(N-methyl-N-(4-pyridine)amino)-N-[N-(1S)-1-ethoxycarbonyl-3-phenylpropyl]-L-alanyl]glycine

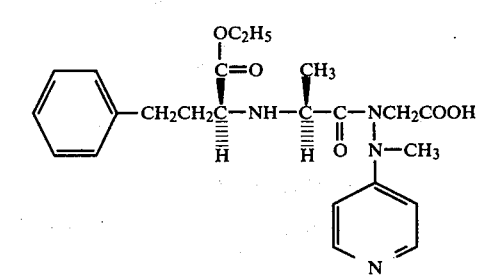

(XI-A) N-(N-phenylamino)-N-[N-(1S)-1-ethoxycarbonyl-3-phenylpropyl]-L-alanyl]glycine

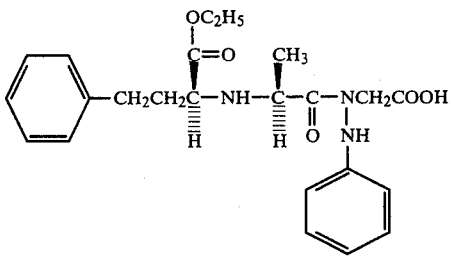

(XII-A) N-(N-methylanilino)-N-[N-(1S)-1-ethoxycarbonyl-2-phenoxyethyl]-L-alanyl]glycine

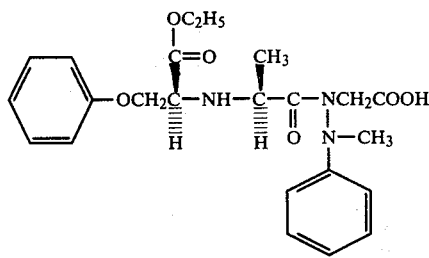

What is claimed is:
1. Compounds of the formula (1)

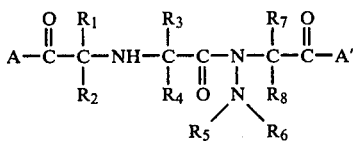

and their pharmaceutically-acceptable salts, wherein
A and A' are independently hydroxy, alkoxy, alkenoxy, aryloxy, arylalkylamino, or hydroxyamino;
$R_1$, $R_2$, $R_7$, and $R_8$ are independently hydrogen, alkyl, aryl, aralkyl, fused cycloalkyl-aryl, fused arylcycloalkyl, aryloxyalkyl, or arylalkyloxyalkyl;
$R_3$ and $R_4$ are independently hydrogen, lower alkyl, lower alkenyl, lower alkynyl, aryl, fused cycloalkyl-aryl, fused aryl-cycloalkyl, fused cycloalkylaryl-alkyl, fused arylcycloalkyl-alkyl, aralkyl, cycloalkyl, or heterocyclic;
$R_5$ and $R_6$ are independently hydrogen, alkyl, alkenyl, alkynyl, acyl, cycloalkyl, cycloalkyl-alkyl, polycycloalkyl, polycycloalkyl-alkyl, aryl, aralkyl, fused cycloalkyl-aryl, fused arylcycloalkyl, fused arylcycloalkyl-alkyl, or fused cycloalkyl-aryl-alkyl;
wherein the alkyl, alkoxy, alkenoxy, alkenyl, and alkynyl groups may carry substituents selected from the group consisting of hydroxy, acyloxy, aryl, alkoxy, aryloxy, halo, amino, mono- or dialkylamino, acylamino, thio, and alkylmercapto; the cycloalkyl rings may include a hetero atom, may be saturated or unsaturated, and may carry substituents selected from the group consisting of alkyl, halo, haloalkyl, hydroxy, alkylamino, and nitro; and the aryl rings may contain a hetero atom and may carry substituents selected from the group consisting of carboxylic acid, cyano, carbo-lower alkoxy, alkyl, hydroxy, alkoxy, hydroxyalkyl, halo, haloalkyl, thio, alkylmercapto, thioalkyl, amino, alkylamino, aminoalkyl, nitro, methylenedioxy, and sulfonylamino;

wherein the alkyl groups contain 1 to 9 carbon atoms; and the cycloalkyl groups and the cycloalkyl portions of substituents containing cycloalkyl groups contain 3 to 9 carbon atoms.

2. The compounds of claim 1 wherein at least one of $R_2$, $R_4$, $R_7$ and $R_8$ is hydrogen.

3. The compounds of claim 2 wherein A and A' are independently hydroxy or lower alkoxy.

4. The compounds of claim 3 wherein $R_1$ is lower alkyl, aryl, or aryl-lower alkyl.

5. The compounds of claim 3 wherein $R_3$ is hydrogen, lower alkyl, or amino-lower alkyl.

6. Compounds according to claim 1 of the formula

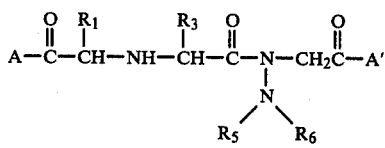

and their pharmaceutically acceptable salts wherein

A and A' are independently hydroxy or lower alkoxy;

$R_1$ is alkyl, arylalkyl, aryloxyalkyl, or arylalkyloxyalkyl; and $R_3$ is alkyl, arylalkyl, or w-amino alkyl.

7. The compound of claim 6 which is N-(N-methylanilino)-N-[N-[(1S)-1-ethoxycarbonyl-3-phenylpropyl]-L-alanyl]glycine t-butyl ester.

8. The compound of claim 6 which is N-(N-methylanilino)-N-[N-[(1S)-1-ethoxycarbonyl-3-phenylpropyl]-L-alanyl]glycine dihydrochloric acid salt.

9. The compound of claim 6 which is N-(N-ethylbenzylamino-N-[N-[(1S)-1-ethoxycarbonyl-3-phenylpropyl]-L-alanyl]glycine.

10. The compound of claim 6 which is N-(N-methylanilino)-N-[N-[(1S1)-1-ethoxycarbonyl-3-phenylpropyl]-L-lysinyl]-glycine.

11. The compound of claim 6 which is N-(N-methylanilino)-N-[N-[(1S)-1-ethoxycarbonyl-ethyl]-L-alanyl]glycine.

12. The compound of claim 6 which is N-(dimethylamino)-N-[N-[(1S)-1-ethoxycarbonyl-3-phenylpropyl]-L-alanyl]glycine.

13. The compound of claim 6 which is N-(N-methyl-N-(4-pyridine)amino)-N-[N-(1S)-1-ethoxycarbonyl-3-phenylpropyl]-L-alanyl]glycine.

14. The compound of claim 6 which is N-(N-phenylamino)-N-[N-(1S)-1-ethoxycarbonyl-3-phenylpropyl]-L-alanyl]glycine.

15. The compound of claim 6 which is N-(N-methylanilino)-N-[N-(1S)-1-ethoxycarbonyl-2-phenoxyethyl]-L-alanyl]-glycine.

16. A pharmaceutical preparation for alleviating hypertension comprising at least one compound or salt according to claim 1 in association with a pharmaceutically acceptable carrier.

17. A method of alleviating hypertension comprising administering to a host suffering therefrom a therapeutically effective amount of at least one compound or salt according to claim 1.

* * * * *